(12) United States Patent
Merkel et al.

(10) Patent No.: US 7,112,708 B2
(45) Date of Patent: Sep. 26, 2006

(54) METHOD OF MAKING DIFLUOROMETHANE, 1,1,1-TRIFLUOROETHANE AND 1,1-DIFLUOROETHANE

(75) Inventors: Daniel C Merkel, West Seneca, NY (US); Hsuehsung Tung, Getzville, NY (US); Ian Shankland, Randolph, NJ (US)

(73) Assignee: Honeywell International Inc., Morristown, NJ (US)

( * ) Notice: Subject to any disclaimer, the term of this patent is extended or adjusted under 35 U.S.C. 154(b) by 157 days.

(21) Appl. No.: 10/816,447

(22) Filed: Apr. 1, 2004

(65) Prior Publication Data

US 2005/0222472 A1 Oct. 6, 2005

(51) Int. Cl.
*C07C 17/20* (2006.01)
*C07C 17/21* (2006.01)
*C07C 17/93* (2006.01)

(52) U.S. Cl. ............... 570/167; 570/164; 570/165; 570/166

(58) Field of Classification Search ........... 570/167, 570/164, 165, 166
See application file for complete search history.

(56) References Cited

U.S. PATENT DOCUMENTS

| | | | |
|---|---|---|---|
| 2,744,148 A | 5/1956 | Ruh et al. | 260/653 |
| 2,745,886 A | 5/1956 | Ruh et al. | 260/653 |
| 2,749,274 A | 6/1956 | Ruh et al. | 260/653 |
| 2,749,375 A | 6/1956 | Ruh et al. | 260/653 |
| 3,862,995 A | 1/1975 | Martens et al. | 200/653.6 |
| 4,147,733 A | 4/1979 | Fishe et al. | 260/653.4 |
| 5,208,395 A | 5/1993 | Elsheikh | 570/166 |
| 5,672,786 A | 9/1997 | Bonniface et al. | 570/165 |
| 6,080,899 A | 6/2000 | Bradley et al. | |
| 6,242,659 B1 | 6/2001 | Requieme et al. | |

FOREIGN PATENT DOCUMENTS

EP 0712826 5/1996

*Primary Examiner*—Elvis O. Price
(74) *Attorney, Agent, or Firm*—Colleen Szuch

(57) ABSTRACT

A process for the production of difluoromethane (HFC-32), 1,1,1-trifluoroethane (HFC-143a) and 1,1-difluoroethane (HFC-152a). In the process the following steps are employed:

(a) providing a reaction vessel,
(b) providing in the reaction vessel activated carbon impregnated with a strong Lewis acid fluorination catalys selected from halides of As, Sb, Al, Tl, In, V, Nb, Ta, Ti, Zr and Hf,
(c) activating the catalyst by passing through the activated carbon impregnated with a strong Lewis acid fluorination catalyst anhydrous hydrogen fluoride gas and chlorine gas,
(d) contacting, in a vapor state in the reaction vessel containing the activated catalyst, hydrogen fluoride and one or more halogenated hydrocarbons selected from chlorofluoromethane, dichloromethane, 1,1,1-trichloroethane, vinyl chloride, 1,1-dichloroethylene, 1,2-dichloroethylene, 1,2-dichloroethane, and 1,1-dichloroethane for a time and at a temperature to produce a product stream comprising hydrofluorocarbon product(s) corresponding to the chlorinated hydrocarbon reactant(s), and one or more of hydrogen chloride, unreactacted chlorinated hydrocarbon reactant(s), under-fluorinated intermediates, and unreacted hydrogen fluoride, and
(e) separating the hydrofluorocarbon product(s) from the product stream.

22 Claims, No Drawings

METHOD OF MAKING DIFLUOROMETHANE, 1,1,1-TRIFLUOROETHANE AND 1,1-DIFLUOROETHANE

FIELD OF THE INVENTION

This invention relates to improved methods for the manufacture of difluoromethane (HFC-32), 1,1,1-trifluoroethane (HFC-143a) and 1,1-difluoroethane (HFC-152a) that are more economical and less corrosive than existing manufacturing methods. Additionally, the invention produces refrigerants via a low temperature vapor phase method that will be more selective towards the desired product than current manufacturing methods.

BACKGROUND TO THE INVENTION

Mechanical refrigeration systems, and related heat transfer devices such as heat pumps and air conditioners, using refrigerant liquids are well known in the art for industrial, commercial and domestic uses. Chlorofluorocarbons (CFCs) were developed in the 1930s as refrigerants for such systems. However, since the 1980s the effect of CFCs on the stratospheric ozone layer has become the focus of much attention. In 1987 a number of government signed the Montreal Protocol to protect the global environment setting forth a timetable for phasing out the CFC products. Subsequent amendments to this protocol accelerated the phase-out of these CFCs and also scheduled the phase-out of HCFCs. Thus, there is a requirement for a non-flammable, non-toxic alternative to replace these CFCs and HCFCs. In response to such demand industry has developed a number of hydrofluorocarbons (HFCs), which have a zero ozone depletion potential.

Hydrofluorcarbons such as difluoromethane (HFC-32), 1,1,1-trifluoroethane (HFC-143a) and 1,1-difluoroethane (HFC-152a) have essentially no ozone depletion potential (ODP) and low global warming potential (GWP), and therefore, they have been found to be acceptable refrigerants and, in some cases, as potential blowing agents in the production of plastic foams.

There are already known methods in the literature to produce HFC-32. U.S. Pat. Nos. 2,749,374 and 2,749,375 disclose a process wherein dichloromethane (HCC-30) is reacted with HF in a liquid phase at a temperature within the range from 110° to 175° C. in the presence of an fluorine containing antimony halide catalyst to obtain HFC-32. In this process, however, a large amount of R-40 series compounds such as monochloromethane and fluoromethane, which are undesired impurities other than R-30 series compounds (HFC-32, HCFC-31 and HCC-30), are formed as by-products. It is also well known in the art that liquefied HF and antimony halide mixtures are very corrosive to metals and alloys.

U.S. Pat. No. 2,745,886 discloses a vapor phase process for fluorinating a variety of halohydrocarbons including HCC-30, which utilizes a hydrated chromium fluoride catalyst activated with oxygen. Similarly, U.S. Pat. No. 2,744,148 discloses a halohydrocarbon fluorination process in which an HF-activated alumina catalyst is used. U.S. Pat. No. 3,862,995 discloses the vapor phase production of HFC-32 by reacting methylene chloride and HF in the presence of a vanadium derivative catalyst supported on carbon. U.S. Pat. No. 4,147,733 discloses a vapor phase reaction for the production of HFC-32 by HCC-30 with HF in the presence of a metal fluoride catalyst. U.S. Pat. No. 5,672,786 discloses a vapor phase reaction for the production of HFC-32 by contacting HCC-30 with HF in the presence of a fluorination catalyst selected from the group consisting of the oxide, fluoride or oxyfluoride of at least one of chromium, aluminum, zinc, nickel, cobalt, copper and magnesium to produce a product stream comprising HFC-32, HCFC-31 and unreacted starting materials.

In U.S. Pat. No. 5,208,395 there is disclosed a vapor phase reaction for the production of HFC-32 by contacting HCC-30 with HF in the presence of certain relatively weak Lewis acid catalysts, such as tin (IV) and bismuth (III) salts, preferably chlorides, and especially tin tetrafluoride, on activated carbon.

There are various drawbacks with these processes. All of these processes require relatively high temperatures of between 200° C. to about 600° C. to make appreciable amounts of product. In practice, these processes for HFC-32 production suffer from a variety of problems including low product yield and poor product selectivity, as well as operational difficulties such as feed decomposition and the reaction mixture and environment can be highly corrosive.

There is a need for a process for the production of difluoromethane (HFC-32), 1,1,1-trifluoroethane (HFC-143a) and 1,1-difluoroethane (HFC-152a) that are more economical and less corrosive than existing manufacturing methods and provides for the production of desired product(s) in good yield and selectivity even at relatively low temperatures. The relatively lower reaction temperatures than that of the previous inventions would enable one to minimize the problem of feed decomposition and corrosion.

SUMMARY OF THE INVENTION

The invention comprises a process for the production of at least one hydrofluorocarbon selected from difluoromethane (HFC-32), 1,1,1-trifluoroethane (HFC-143a) and 1,1-difluoroethane (HFC-152a), wherein the process is a vapor phase process comprising:

(a) providing a reaction vessel, (b) providing in the reaction vessel activated carbon impregnated with a strong Lewis acid fluorination catalyst wherein the strong Lewis acid catalyst is selected from halides of As, Sb, Al, Tl, In, V, Nb, Ta, Ti, Zr and Hf, (c) activating the catalyst by passing through the activated carbon impregnated with a strong Lewis acid fluorination catalyst anhydrous hydrogen fluoride gas and chlorine gas, (d) contacting, in a vapor state in the reaction vessel containing the activated catalyst, hydrogen fluoride and one or more halogenated hydrocarbons selected from the group consisting of chlorofluoromethane, dichloromethane, 1,1,1-trichloroethane, vinyl chloride, 1,1-dichloroethylene, 1,2-dichloroethylene, 1,2-dichloroethane, and 1,1-dichloroethane for a time and at a temperature to produce a product stream of hydrofluorocarbon product(s) corresponding to the chlorinated hydrocarbon reactant(s), hydrogen chloride, unreactacted chlorinated hydrocarbon reactant(s), and unreacted hydrogen fluoride, and (e) separating the hydrofluorocarbon product(s) from the product stream.

DETAILED DESCRIPTION OF THE INVENTION AND PREFERRED EMBODIMENTS

In general, the process of this invention comprises providing a vapor phase fluorination catalyst by impregnating activated carbon with a strong Lewis acid fluorination catalyst. The prepared supported fluorination catalyst is then loaded into any suitable reaction vessel, such as a metal tube or pipe reactor, to make a catalyst bed. The reaction vessel is preferably constructed from materials that are resistant to the corrosive effects of hydrogen fluoride, such as nickel and nickel containing alloys such as Hastelloy®, Inconel®, and Monel®. Alternatively, a reaction vessel lined with fluoropolymers would be suitable also. The catalyst loaded activated carbon bed is then activated. The activation processes is to pass $Cl_2$ gas and anhydrous hydrogen fluoride (AHF) gas over the bed at moderate temperatures of from about 20° C. to about 400° C., more preferably between about 40° C. to about 300° C. and, most preferably, between about 50° C. and about 200° C. Any suitable amount of chlorine gas and anhydrous hydrogen fluoride sufficient to effectively activate the fluorination catalyst may be employed for this purpose. In general, a minimum of about 1 mole of chlorine gas per mole of fluorination catalyst is employed for activation of the catalyst. Generally the amount of chlorine gas employed for this purpose is from about 1 mole to about 10 moles, preferably from about 2 moles to about 8 moles, and especially about 3 moles to about 5 moles, of chlorine gas per mole of catalyst. In general, a minimum of about 3 mole of anhydrous hydrogen fluoride gas per mole of fluorination catalyst is employed for activation of the catalyst. Generally the amount of anhydrous hydrogen fluoride gas employed for this purpose is from about 3 mole to about 10 moles, preferably from about 3 moles to about 8 moles, and especially about 3 moles to about 5 moles, of anhydrous hydrogen fluoride gas per mole of catalyst.

Any suitable strong Lewis acid fluorination catalyst may be employed in the process of this invention. The preferred catalyst is selected from a group of halides of As, Sb, Al, Tl, In, V, Nb, Ta, Ti, Zr and Hf; more preferably is Sb and As halides, and most preferably Sb(V) halides supported on the activated carbon. The amount of catalyst employed will be any suitable catalytically effective amount sufficient to convert the halogenated hydrocarbon reactant to hydrofluorocarbon product in the gaseous phase reaction of this invention.

The halogenated hydrocarbon reactant employed in the process of this invention may be any suitable halogenated hydrocarbon reactant suitable for conversion to the desired hydrofluorocarbon product in the gaseous phase reaction of this invention. Examples of such suitable halogenated hydrocarbon reactants include a halogenated hydrocarbon or a mixture of two or more halogenated hydrocarbons selected from a group of chlorofluoromethane, dichloromethane ("HCC-30") and 1,1,1-trichloroethane (HCC-140a), vinyl chloride, 1,1-dichloroethylene, 1,2-dichloroethylene, 1,2-dichloroethane, and 1,1-dichloroethane. Preferably, the halogenated hydrocarbon reactant is chlorofluoromethane, methylene chloride, 1,1,1,-trichloroethane, 1,1-dichloroethylene and vinyl chloride. The halogenated hydrocarbon or a mixture of two or more halogenated hydrocarbons is contacted with HF in the presence of the activated carbon supported Lewis acid fluorination catalyst in the reaction vessel to produce a product stream of corresponding hydrofluorocarbon, hydrogen chloride ("HCl"), unreacted starting material, and unreacted hydrogen fluoride ("HF"). The desired hydrofluorocarbon product(s) is separated from the product stream, generally in substantially pure form. The ratio of hydrogen fluoride reactant to halogenated hydrocarbon reactant employed in the process of this invention will generally be 2: or greater. Generally, this ratio will be from about 2: to about 50:1, preferably from about 2:1 to about 30:1, and more preferably from about 2:1 to about 20:1.

Before the hydrogen fluoride and chlorinated hydrocarbon reactants are introduced into the reaction vessel these reactants may be preheated, if desired. The preheating temperature will generally vary with the chlorinated hydrocarbon reactant employed. Basically the hydrogen fluoride and chlorinated hydrocarbon reactants must be in the gaseous (vapor) phase prior to entering the reaction zone. This preheating step may also be employed to provide vaporized, superheated reactant feeds to some extent, although this is not necessary. The preheating of the reactant feeds will generally be sufficient to heat them to about the reaction temperature before they enter the reaction zone. The temperature maintained in the reaction zone in the reaction vessel will generally be in a range of from about 40° C. to about 400° C., preferably in a range of from about 50° C. to about 300° C., more preferably in a range of from about 50° C. to about 250° C., and most preferably in a range of from about 60° C. to about 200° C.

The pressure employed in the reaction zone is generally not critical and may be at atmospheric, super-atmospheric or under vacuum. Generally a pressure of between about 5 psia to about 215 psai, preferably from about 10 psia to about 180 psia, and preferably from about 15 psia to about 115 psia will be employed. Most preferably, the reaction is conducted at between 15 psia and 115 psia.

Contact time, the time required for the reactants to pass through the catalyst bed assuming a 100% void catalyst bed, is typically from about 1 to about 120 seconds, preferably from about 2 to 60 seconds, more preferably from about 4 to about 50 seconds, and most preferably from about 5 to about 30 seconds. The reaction may be conducted as either a batch reaction or as a continuous reaction. Generally it is preferred to conduct the reaction as a continuous reaction.

In order to maintain good catalyst activity of the catalyst in the reaction vessel, it will generally be preferred to co-fed chlorine gas to the reaction vessel with the hydrogen fluoride and chlorinated hydrocarbon reactant feeds. When the reaction is conducted as a continuous reaction, the amount of chlorine gas co-fed to the reaction zone will be a minimum of about 0.005 mole of chlorine gas per mole of organic reactant feed. Generally, the amount of chlorine gas co-fed to the reaction zone for this purpose in a continuous reaction will be from about 0.005 mole to about 0.1 mole, preferably from about 0.01 mole to about 0.05 mole, more preferably from about 0.01 mole to about 0.025 mole, of chlorine gas per mole of organic reactant feed. If the reaction is conducted as a batch reaction, the amount of chlorine gas co-feed employed for this purpose will be a minimum of about 1 mole of chlorine gas per mole of Lewis acid fluorination catalyst. Generally, the amount of chlorine gas co-fed to the reaction zone for this purpose in a batch reaction will be from about 1 mole to about 10 moles, preferably from about 2 moles to about 8 moles, and more preferably from about 3 moles to about 5 moles, per mole of Lewis acid fluorination catalyst.

In another aspect of this invention, the under-fluorinated intermediates in the product stream, from which the desired hydrofluorocarbon product(s) have been separated, may be, and preferably are, fed back to the reaction zone of the reaction vessel. It is also desirable to recycle unreacted reactants from the product stream, from which the desired hydrofluorocarbon product(s) have been separated, back to the reaction zone of the reaction vessel.

Any suitable method of separating the desired hydrofluorocarbon product from the product stream may be employed, such as, for example, distillation.

The invention is illustrated by, but not limited to, the following examples.

EXAMPLE 1

The vapor phase fluorination reaction was conducted in a 2.54 cm diameter×81 cm long Monel® reactor. The reactor was heated with an electric furnace. The reactor was preceded by a vaporizer, which was also heated electrically, that ensured that all the reactor feeds were in the gaseous state before entering the reaction zone. The reactor was loaded with 242 ml of $SbCl_5$ supported catalyst that was prepared and activated by the following method. This $SbCl_5$ catalyst was prepared by impregnating $SbCl_5$ (169 g) on Calgon PCB (4×10 mesh) activated carbon (340 ml). It was charged to the reactor and activated in the reactor before use. Activation procedures were as follows. First, nitrogen of 20 ml/min was flowed over the catalyst. In this nitrogen atmosphere, the reactor was heated to 100° C. Then, anhydrous HF and chlorine were allowed to flow through the reactor at 0.25 g/min and 0.3 g/min, respectively, for 1 hour. After the hour passed the chlorine flow was discontinued while HF and $N_2$ continued to flow through the catalyst bed. The flow rate of the chlorine was measured using a Hastings mass flow meter and controller. The flow rate of HF was controlled and measured by a Porter Liquiflow mass flow meter connected to Honeywell PlantScape DCS (Distributive Control System) and confirmed by the weight change in the source cylinder.

With the reactor temperature already at 100° C. and atmospheric pressure, the HF flow was increased to 1.0 g/min at which time the $N_2$ flow was stopped. HF feed alone was passed over the catalyst at this rate for about a ½ hour to ensure complete activation of the catalyst before methylene chloride (HCC-30) feed was started at a rate of about 0.31 g/min. This provided a mole ratio of HF to HCC-30 of between about 7:1–8:1. The flow rate for the reactants, HCC-30 and HF, were measured with Porter Liquiflow mass flow meters and controlled by a Honeywell PlantScape DCS (Distributive Control System) and confirmed by the weight change in the respective source cylinders. The contact time was about 9 seconds. Contact time is defined as bulk volume (in ml) of catalyst divided by volumetric flow rate of reactants (in ml/sec). The reactor output was sampled directly into an in-line GC, i.e., a Perkin Elmer 8500 gas chromatograph using a Fluorocol column and FID detector, so that the amounts of organic species exiting the reactor could be determined during the operation of the process. The vapor phase reaction proceeded quite nicely at 100° C. and atmospheric pressure. The conversion of HCC-30 at these conditions was 95.16% on a molar basis. The selectivity of HFC-32 based on mole% was 96.66% and the intermediate HCFC-31 had a selectivity of 2.18%.

EXAMPLE 2

The catalyst was subjected to the same preparation and activation procedure as described in Example 1. The reactor was then heated to 180° C. at atmospheric pressure and the HF and HCC-30 feeds were restarted at the same rates as in Example 1. The new contact time was about 7.25 seconds. The reaction was run at these conditions for about 9 hours during which time the reactor output was again sampled directly into an in-line GC. The conversion of HCC-30 on a molar basis was 96.74%. The selectivity of HFC-32 based on mole% was 96.93% and the intermediate HCFC-31 had a selectivity of 2.16%. The main impurity seen by GC/MS was HCC-40 whose selectivity was 0.88 mole %.

EXAMPLE 3

The vapor phase fluorination reaction is conducted in the same 2.54 cm diameter×81 cm long Monel® reactor preceded by a vaporizer as in Examples 1 and 2. The reactor is heated with an electric furnace. The reactor is loaded with 100 ml of $SbCl_5$ supported catalyst that is prepared and activated by the same procedures as described in Example 1. The reactor is kept at 100° C. and at atmospheric pressure. The HF flow rate is adjusted to 0.35 g/min and the 1,1-dichloroethylene (VDC) is started at 0.28 g/min. This provides a mole ratio of HF to VDC of about 8:1. The contact time is about 10 seconds. The reaction is run at these conditions until stable reaction conditions are reached. The reaction is monitored by taking reactor effluent samples directly into an in-line GC as described in Examples 1 and 2. The conversion of the VDC is >95% on a molar basis. The desired HFC-143a product is produced in good yields (>80% on a molar basis) at these conditions with the majority of the other products being intermediates HCFC-141b and HCFC-142b.

EXAMPLE 4

In a procedure similar to that described in the previous Examples, when vinyl chloride is employed as the halogenated hydrocarbon reactant 1,1-difluoroethane (HFC-152a) is produced in the catalyzed, vapor phase reaction of this invention.

While the invention has been described herein with reference to the specific embodiments thereof, it will be appreciated that changes, modification and variations can be made without departing from the spirit and scope of the inventive concept disclosed herein. Accordingly, it is intended to embrace all such changes, modification and variations that fall with the spirit and scope of the appended claims.

We claim:

1. A process for the production of at least one hydrofluorocarbon selected from the group consisting of difluoromethane (HFC-32), 1,1,1-trifluoroethane (HFC-143a) and 1,1-difluoroethane (HFC-152a), the process comprising:
   (a) providing a reaction vessel,
   (b) providing in the reaction vessel activated carbon impregnated with a strong Lewis acid fluorination catalyst wherein the strong Lewis acid catalyst is selected from the group consisting of halides of As, Sb, Al, Tl, In, V, Nb, Ta, Ti, Zr and Hf,
   (c) activating the catalyst by passing through the activated carbon impregnated with a strong Lewis acid fluorination catalyst anhydrous hydrogen fluoride gas and chlorine gas,
   (d) contacting, in a vapor state in the reaction vessel containing the activated catalyst, hydrogen fluoride and one or more halogenated hydrocarbons selected from the group consisting of chlorofluoromethane, dichloromethane, 1,1,1-trichloroethane, vinyl chloride, 1,1-dichloroethylene, 1,2-dichloroethylene, 1,2-dichloroethane, and 1,1-dichloroethane for a time and at a temperature to produce a product stream comprising hydrofluorocarbon product(s) corresponding to the chlorinated hydrocarbon reactant(s), and one or more of hydrogen chloride, unreactacted chlorinated hydrocarbon reactant(s), under-fluorinated intermediates, and unreacted hydrogen fluoride, and (e) separating the hydrofluorocarbon product(s) from the product stream.

2. A process according to claim 1 wherein the strong Lewis acid fluorination catalyst is selected from the group consisting of halides of As and Sb.

3. A process according to claim 1 wherein the hydrogen fluoride and chlorinated hydrocarbon reactants in step (d) are preheated to a gaseous stage prior to their introduction into the reaction vessel.

4. A process according to claim 3 wherein the reactants are preheated to a superheated gaseous stage approximating the reaction temperature prior to their introduction into the reaction vessel.

5. A process according to claim 1 wherein the amount of hydrogen fluoride employed to activate the catalyst in step (c) is in the range of from about 3 to about 10 moles of hydrogen fluoride per mole of fluorination catalyst and the amount of chlorine gas employed to activated the catalyst in step (c) is in the range of from about 1 to about 10 moles of hydrogen fluoride per mole of fluorination catalyst.

6. A process according to claim 5 wherein the amount of hydrogen fluoride gas is from about 3 to about 5 moles per mole of fluorination catalyst and the amount of chlorine gas is from about 3 to about 5 moles per mole of fluorination catalyst.

7. A process according to claim 1 wherein the reaction is conducted continuously and at least about 0.005 mole of chlorine gas per mole of chlorinated hydrocarbon reactant(s) is co-fed to the reaction vessel in step (d) to maintain catalyst activity.

8. A process according to claim 7 wherein the amount of chlorine gas co-fed to the reaction vessel is from about from about 0.01 to about 0.25 mole gas per mole of chlorinated hydrocarbon reactant(s).

9. A process according to claim 1 wherein the reaction is conducted as a batch reaction and least about 1 mole of chlorine gas per mole of fluorination catalyst is introduced into the reaction vessel in step (d) to maintain catalyst activity.

10. A process according to claim 9 wherein a mount of chlorine gas introduced into the reaction vessel is from about from about 3 to about 5 moles gas per mole of fluorination catalyst.

11. A process according to claim 1 wherein the ratio of the amount of hydrogen fluoride to the amount of halogenated hydrocarbon reactant(s) in step (d) is at least 2:1.

12. A process according to claim 11 wherein the ratio of hydrogen fluoride to the amount of halogenated hydrocarbon reactant(s) in step (d) is from about 2:1 to about 20:1.

13. A process according to claim 1 wherein the reaction in step (d) is conducted at a temperature within the range of from about 40° C. to about 400° C.

14. A process according to claim 13 wherein the temperature is within the range of from about 60° C. to about 200° C.

15. A process according to claim 1 wherein reaction in step (d) is conducted at a pressure of from about 10 psia to about 180 psia.

16. A process according to claim 1 wherein the chlorinated hydrocarbon reactant in step (d) comprises methylene chloride and the hydrofluorocarbon product comprises difluoromethane.

17. A process according to claim 1 wherein the halogenated hydrocarbon reactant in step (d) comprises at least one of 1,1-dichloroethylene and 1,1,1-trichloroethane and the hydrofluorocarbon product comprises 1,1,1-trifluoroethane.

18. A process according to claim 1 wherein the chlorinated hydrocarbon reactant in step (d) comprises vinyl chloride and the hydrofluorocarbon product comprises 1,1-difluoroethane.

19. A process according to claim 1 wherein the reaction in step (d) is conducted as a continuous reaction and under-fluorinated intermediates in the product stream, from which the hydrofluorocarbon product has been separated, is recycled back to the reaction vessel.

20. A process according to claim 1 wherein the hydrofluorocarbon product separated from the product stream is substantially pure hydrofluorinated product.

21. A process according to claim 1 wherein the Lewis acid fluorination catalyst comprises Sb(V) halides.

22. A process according to claim 21 wherein the amount of hydrogen fluoride employed to activate the catalyst in step (c) is in the range of from about 3 to about 10 moles of hydrogen fluoride per mole of fluorination catalyst and the amount of chlorine gas employed to activated the catalyst in step (c) is in the range of from about 1 to about 10 moles of chlorine per mole of fluorination catalyst, the hydrogen fluoride and halogenated hydrocarbon reactants in step (d) are preheated to a gaseous stage prior to their introduction into the reaction vessel, the ratio of hydrogen fluoride to the amount of halogenated hydrocarbon reactant(s) in step (d) is from about 2:1 to about 20:1, the reaction in the reaction vessel is conducted at a temperature within the range of about 60° C. to about 200° C. and a pressure of atmospheric pressure, and the halogenated hydrocarbon reactant(s) is selected from the group consisting of chlorofluoromethane, dichloromethane, 1,1,1-trichloroethane, 1,1-dichloroethylene, vinyl chloride and 1,1-dichloroethane.

\* \* \* \* \*